United States Patent [19]

De Clippeleir et al.

[11] 4,451,686

[45] May 29, 1984

[54] DEHYDROGENATION PROCESS

[75] Inventors: Georges E. M. J. De Clippeleir; Raymond M. Cahen, both of Brussels; Francisco A. Martins Mendes Cerejo, Ecaussinnes, all of Belgium

[73] Assignee: Cosden Technology, Inc., Dallas, Tex.

[21] Appl. No.: 492,527

[22] Filed: May 9, 1983

[51] Int. Cl.$^3$ ................................................ C07C 5/36
[52] U.S. Cl. .................................. 585/444; 585/654; 502/61; 502/64
[58] Field of Search .................. 585/444, 654; 502/61, 502/64

[56] References Cited

U.S. PATENT DOCUMENTS

| | | | |
|---|---|---|---|
| 4,061,724 | 12/1977 | Grose et al. | 423/335 |
| 4,073,865 | 2/1978 | Flanigen et al. | 423/335 |
| 4,309,275 | 1/1982 | Mulaskey | 208/109 |
| 4,325,929 | 4/1982 | Young | 423/339 |
| 4,344,927 | 8/1982 | Young | 423/339 |
| 4,400,571 | 8/1983 | Robinson | 585/480 |

FOREIGN PATENT DOCUMENTS 2075045 11/1981 United Kingdom ................ 208/109

*Primary Examiner*—Delbert E. Gantz
*Assistant Examiner*—A. Pal
*Attorney, Agent, or Firm*—Robert H. Sproule; M. Norwood Cheairs; Michael J. Caddell

[57] ABSTRACT

Catalytic dehydrogenation of alkyl- or dialkyl- aromatic hydrocarbons such as ethylbenzene or ethyltoluene to vinyl aromatic hydrocarbons is achieved by passing the aromatic hydrocarbons on a crystalline silica which has been calcined under an inert atmosphere and which contains from about 0.05 to about 1 weight percent of an alkali metal oxide such as sodium oxide. In the preparation of the crystalline silica, limited washing of the crystalline silica precursor is performed to obtain an amount of alkali metal oxide remaining in the crystalline silica between about 0.05 and about 1 weight %.

22 Claims, No Drawings

DEHYDROGENATION PROCESS

BACKGROUND OF THE INVENTION

The present invention relates to a process for producing vinyl aromatic hydrocarbons by dehydrogenation of alkylaromatic hydrocarbons. More specifically, the invention is directed to the dehydrogenation of ethylbenzene and ethyltoluene to vinylbenzene and vinyltoluene respectively.

Catalytic dehydrogenation of alkyl or dialkylaromatic hydrocarbons is one of the commercial processes presently employed for the manufacture of vinyl aromatic hydrocarbons, products which are extensively used for the further production of homopolymers and copolymers. In these dehydrogenation processes, the feed mixture contains alkyl or dialkyl aromatic hydrocarbons and an inert diluent in the vapor phase. The dehydrogenation reaction may be executed by passing the feed mixture either through a single reactor or through two successive reactors. In this latter case, the reaction mixture is reheated before entering the second reactor. The inert diluent, preferably steam, supplies heat to the endothermic reaction and favors the production of the vinyl aromatic hydrocarbons. For example, ethylbenzene is vaporized, heated and then passed together with steam through the dehydrogenation reactor(s) containing a suitable catalyst. The feed mixture is generally introduced at a temperature higher than 600° C. resulting in some thermocracking of ethylbenzene. The dehydrogenation reaction produces styrene and additional by-products including benzene, toluene, tar products and coke. The final product yield is accordingly affected by the production of these unwanted by-products.

The catalysts used in these dehydrogenation processes generally contain one or more oxides of iron, chromium or zinc, and a smaller amount of an alkali metal oxide, particularly potassium oxide; it has been found that potassium oxide promotes the removal of coke and tars by reaction with steam through the water-gas reaction, and mitigates therefore a carbon build-up on the catalyst surface. In recent years, improved catalysts of this general type consisting of mixtures of metal oxides have been described. They provide a selectively with respect to the vinyl aromatic hydrocarbon in the range from about 85 mole percent to about 95 mole percent, depending on the feed, for a conversion of the ethyl aromatic hydrocarbon in the 40 to 45 mole percent range after the first step, and about 60 to 70 mole percent after the second step.

Many attempts to improve the overall yield of vinyl aromatic hydrocarbons by catalytic dehydrogenation of hydrocarbon feed stocks have been reported. These recent works are more particularly directed to the use of new catalysts in order to improve this selectivity; for example, it was expected that aluminosilicate zeolites would be more selective than the previously used catalysts. Previous experiments have been conducted utilizing these catalysts, typically Nax and NaY zeolites impregnated with chromium compounds, for the dehydrogenation of ethylbenzene; however, their selectivity with respect to vinylbenzene did not exceed 60%.

A crystalline silica composition having a uniform pore structure but not exhibiting ion exchange properties was disclosed in U.S. Pat. No. 4,061,764 by Grose, wherein the crystalline silica was useful for the separation of p-xylene from o-xylene, m-xylene and ethylbenzene, and for selectivity absorbing organic materials from water.

SUMMARY OF THE INVENTION

In order to overcome the problems, including lack of selectivity, of the previous dehydrogenation processes, there is provided in accordance with the present invention, a process for producing vinyl aromatic hydrocarbons by dehydrogenation of the corresponding alkyl aromatic hydrocarbons. The process comprises passing the alkyl aromatic hydrocarbons on a crystalline silica which has been calcined under inert atmosphere and which contains from about 0.05 to about 1 wt% alkali metal oxides, at a temperature between about 500° C. and about 650° C.

The crystalline silica is obtained by hydrothermal crystallization of a reaction mixture containing water, a source of silica, and an alkylonium compound having the formula:

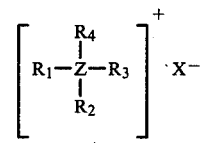

wherein $R_1$, $R_2$, $R_3$ and $R_4$ are alkyl radicals, Z is either phosporus or nitrogen and X is $OH^-$ or the radical of a monovalent acid, at a pH between about 7 and 14, to form a hydrous crystalline precursor. The hydrous crystalline precursor is washed with water and then washed with a strong acid, then dried and calcined in an inert atmosphere. The crystalline silica is not submitted to any further washing in order to obtain an amount of alkali metal oxides remaining therein between 0.5% and 1 wt%.

Those familiar with the art of catalysis know that even minor variations in compositions and/or in method of their manufacture may result in significant and unexpected variations in the behavior of the catalyst for a given reaction. The main factors to be considered, however, are the activity, the selectivity and the stability of the catalyst. An object of the present invention, therefore, is to provide a novel process for producing vinyl aromatic hydrocarbons by dehydrogenation of the corresponding alkyl aromatic hydrocarbons to obtain superior overall yields of vinyl aromatic hydrocarbons. One of the more specific objects is to provide a catalytic process of improved activity and selectivity with respect to the dehydrogenation of alkyl or dialkyl aromatic hydrocarbons to the corresponding vinyl hydrocarbons. A further object of the invention is to increase the production capacity of a given dehydrogenation unit. The particular object of the invention is to provide a process for dehydrogenating ethylbenzene and ethyltoluene to obtain higher overall yields in vinylbenzene and vinyltoluene.

DETAILED DESCRIPTION OF THE PREFERRED EMBODIMENTS

In accordance with this invention, it has been found that improved overall yields of vinyl aromatic hydrocarbons are achieved when the corresponding alkyl aromatic hydrocarbons are contacted under dehydrogenation reaction conditions with a crystalline silica which contains a residual amount of alkali metal oxides and which has been calcined under an inert atmosphere. Particularly, high overall yields are obtained in accordance with the process of the present invention when ethylbenzene or ethyltoluene are dehydrogenated in the presence of the crystalline silica catalyst. The process of the present invention may also be applied to the dehydrogenation of other alkyl or dialkyl aromatic hydrocarbons, such as isopropylene or diethylbenzene.

The crystalline silica is prepared by hydrothermal crystallization of a reaction mixture containing water, a source of silica, and a water-soluble alkylonium compound having the formula:

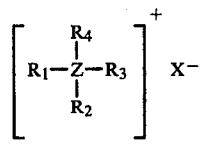

wherein $R_1$, $R_2$, $R_3$ and $R_4$ are alkyl radicals, Z is either phosphorus or nitrogen, and X is $OH^-$ or the radical of a monovalent acid, at a pH between about 7 and about 14, to form a hydrous crystalline precursor. Generally, the alkyl radicals contain from 2 to 6 carbon atoms. As examples of alkylonium compounds, it may be cited tetraalkylammonium hydroxides, tetraalkylphosphonium hydroxides, and the chloride, bromide and iodide salts corresponding to these hydroxides.

The hydrous crystalline precursor is washed first with water and then with a strong acid such as hydrochloric acid, then dried and finally calcined in an inert atmosphere at a temperature between about 450° C. and about 900° C. After calcination, the attained crystalline silica is not submitted to any further washing to avoid loss of the residual alkali metal oxide located therein.

The alkali metal oxide may result from the silica itself. In other words, the alkali metal oxide may exist in sufficient quantities as an impurity in the source of silica itself without further treatment. On the other hand, the source of silica may be an alkali metal silicate formed by reacting an alkali metal hydroxide with colloidal silica. In most cases, the residual alkali metal appears as impurities in the crystalline product. Its removal can be carried out if desired by washing with a strong acid after the calcination step or by treatment with an $NH_4^+$ salt. In the process of the present invention, however, it has been found that a limited amount of alkali metal should remain in the crystalline structure. Generally, the residual amount of alkali metal oxide does not exceed about 1% based on the weight of the crystalline silica, and is preferably between about 0.05 and about 0.5%. It has also been observed that a crystalline silica having too high a residual amount of alkali metal oxide therein leads to catalysts of less thermal stability and therefore, lower dehydrogenation activity. Surprisingly, it has been found that calcination under an inert atmosphere has a stabilizing effect on the crystalline structure while such an effect does not appear with calcination under an oxidizing atmosphere.

In U.S. Pat. No. 4,061,724 by Grose, incorporated herein by reference, an alkylonium compound was utilized in the preparation of a silicalite catalyst having no ion exchange characteristics. The silicalite of the Grose patent exhibited hydrophobic tendencies making it a possible candidate for selective removal of organics from waste water.

In order to prepare the crystalline silica of the present invention, the reaction mixture will contain from 150 to 700 moles water, from 13 to 50 moles of non-crystalline $SiO_2$, and from 0.3 to 6.5 moles of $M_2O$ wherein M is an alkali metal, per mole of quaternary ammonium compound or quaternary phosphonium compound. The reaction mixture is maintained at a temperature from about 100° to 250° C. under autogeneous pressure until crystals of the silica are formed, ordinarily in about 50 to about 150 hours. The quaternary compound of the present invention may be produced in situ; for example, a quaternary ammonium chloride may be generated from a alkyl chloride and a tertiary amine.

The crystalline silica of the present invention, prepared in accordance with the particular conditions described above, has an X-ray powder diffraction pattern which is similar to the crystalline silica described in U.S. Pat. No. 4,061,724. The following table lists the data representing the X-ray powder diffraction pattern of a typical crystalline silica compound of the present invention containing from 20 to 40 moles of $SiO_2$ and from about 0.05 to about 1 moles of $Na_2O$ per mole of alkylonium compound.

The alkylonium moeity is occluded in the crystalline silica framework.

TABLE 1

| Distance (Angstroms) | Relative Intensity | Distance (Angstroms) | Relative Intensity |
|---|---|---|---|
| 11.16 | 47 | 3.44 | 13 |
| 10.02 | 29 | 3.35 | 8 |
| 9.78 | 14 | 3.33 | 10 |
| 9.05 | 3 | 3.26 | 4 |
| 7.48 | 11 | 3.19 | 1 |
| 7.09 | 4 | 3.16 | 2 |
| 6.72 | 7 | 3.06 | 12 |
| 6.35 | 13 | 2.99 | 9 |
| 6.06 | 8 | 2.96 | 4 |
| 5.99 | 9 | 2.88 | 1 |
| 5.72 | 7 | 2.80 | 1 |
| 5.58 | 8 | 2.74 | 4 |
| 5.38 | 2 | 2.61 | 5 |
| 5.13 | 4 | 2.58 | 2 |
| 4.99 | 6 | 2.52 | 2 |
| 4.62 | 7 | 2.50 | 5 |
| 4.45 | 8 | 2.42 | 2 |
| 4.38 | 11 | 2.41 | 3 |
| 4.26 | 12 | 2.01 | 7 |
| 4.10 | 3 | 2.00 | 9 |
| 4.01 | 7 | 1.97 | 1 |
| 3.86 | 100 | 1.96 | 2 |
| 3.76 | 27 | 1.92 | 2 |
| 3.73 | 47 | 1.88 | 3 |
| 3.66 | 35 | | |
| 3.60 | 2 | | |
| 3.49 | 3 | | |

It has been found that such a crystalline silica has unexpected catalytic properties in the dehydrogenation of alkyl or dialkyl aromatic compounds. The thermal stability of the crystalline silica of the present invention is an important factor in the product yield from dehydrogenation of alkyl aromatics because it allows the catalyst to be used for longer periods of time, for example more than 500 hours. The further advantage of such a crystalline silica resides in the fact that it is thermally stable up to temperatures as high as 900° C.

Moreover, the yields obtained with the catalyst of the present invention are really quite surprising since the literature teaches that catalytic activity of zeolitic type catalysts is due to the presence of aluminum atoms in the structure of the zeolite and specifically to the number of aluminum atoms present. This position is also discussed in the Dutch patent application No. 80/03142 by Shell Internationale Research Mij, wherein it is shown that a crystalline silica or "silicalite" similar to the one described in U.S. Pat. No. 4,061,724, but which has been calcined in an oxidizing atmosphere and washed with hydrochloric acid to remove the alkali metal oxide impurities, has catalytic activity in aromatization reactions, but that overall yields are improved when the crystalline silica/"silicalite" is used in conjunction with $Al_2O_3$.

The conditions under which dehydrogenation takes place in the present invention can be the conditions under which normal vapor phase catalytic dehydrogenation reactions are performed. Thus, reaction temperatures should be between about 550° C. and 650° C., and preferably between about 580° C. and 630° C. Similarly, pressures may vary widely and can range from subatmospheric, for example 0.1 atmosphere, to superatmospheric, for example 50 atmospheres. Preferably, however, pressures may range from about 0.3 to 3 atmospheres, and more preferably from about 0.4 to 1 atmosphere. The dehydrogenation reaction is generally carried out in the presence of a gaseous diluent which is employed to reduce the partial pressure of the reactants and to control their residence time in the reactor(s). Illustrative of the diluent gases that may be used are helium, nitrogen, carbon dioxide, steam, or mixtures thereof; preferably, however, the diluent is steam or carbon dioxide or mixtures of steam and carbon dioxide.

In a preferred embodiment of the process of the present invention, carbon dioxide is used as a diluent. It has been found that use of carbon dioxide results in improved conversion of the alkyl aromatic hydrocarbons. While not wishing to be found by the theory of operation, it is believed that the use of carbon dioxide increases yields by the inverse water gas shift reaction.

The molar ratio of gases diluent to alkyl or dialkyl aromatic compounds may vary over a wide range from at least about 1 mole to about 25 moles of diluent per mole of alkyl or dialkyl aromatic compounds; however, a molar ratio of from about 5 moles to about 16 moles of diluent to alkyl or dialkyl aromatic compound is more generally used. When operating under low pressures, the molar ratio is preferably between about 5 and about 10.

The rate of feeding the alkyl or dialkyl aromatic hydrocarbon and diluent over the catalyst bed, or in other words, the liquid hourly space velocity (LHSV) (volume of feed per volume of catalyst per hour) may vary widely from about 0.01 to 1.0.

An advantage of the catalyst of the present invention resides in the fact that it is easily regenerated according to known methods in the art; particularly the regeneration includes heating in a nitrogen diluted air stream at 600° C. until exothermicity has ceased.

The following examples are presented in order to be illustrative of the present invention without limiting its scope.

EXAMPLE 1

A catalyst was prepared by mixing 79.2 grams of colloidal silica containing 0.8 wt% $Na_2O$ in 250 grams water with 18 grams of $(C_3H_4)_4N^+Br^-$ in 54 grams $H_2O$; 8.4 grams NaOH in 30 grams $H_2O$ was added to the mixture. During the stirring, the pH of the mixture has varied from 11 to 9. After stirring, the mixture was heated at 150° C. in an autoclave for 3 days. The resulting crystalline silica was calcined at 600° C. under an inert atmosphere of $N_2$. The crystalline silica has a residual amount of $Na_2O$ of 0.5 wt%.

This catalyst was charged in a reactor wherein a mixture of ethylbenzene and carbon dioxide was fed in a molar ratio of ethylbenzene to carbon dioxide of 1:16.

The dehydrogenation reaction was effected under atmospheric pressure, at a temperature of 600° C. with a LHSV of 0.1.

The following results were obtained 50 hours after startup:
conversion of ethylbenzene (wt %): 86.18
selectivity in styrene (wt %): 98.0

EXAMPLE 2

The catalyst prepared in Example 1 was used for dehydrogenation of ethylbenzene under the following conditions:

| gaseous diluent: | $CO_2$ | |
| --- | --- | --- |
| molar ratio of diluent/ethylbenzene: | 13 | |
| temperature: | 600° C. | |
| pressure: | atmospheric | |
| LHSV: | 0.1 | |
| The following results were obtained: | | |
| Time after start-up (hrs): | 170 | 250 |
| Conversion of ethylbenzene (%) | 62.2 | 61.2 |
| Selectivity in styrene (%) | 97.2 | 97.3 |

COMPARISON EXAMPLE 2A

By way of comparison, a catalyst such as that prepared in Example 1 was used, except that the catalyst was calcined for 1 hour at 600° C. in an oxidizing atmosphere and thereafter washed with hydrochloric acid. The residual amount of $Na_2O$ was less than 160 ppm. This catalyst was tested for dehydrogenation of ethylbenzene under the following conditions:

| Gaseous diluent: | $CO_2$ | |
| --- | --- | --- |
| Molar ratio of diluent/ethylbenzene: | 20 (A), | 19 (B) |
| Temperature: | 600° C. | |
| Pressure: | atmospheric | |
| LHSV: | 0.1 | |
| The following results were obtained: | (A) | (B) |
| Time after start-up (hrs) | 22 | 47 |
| Conversion of ethylbenzene (%) | 94.6 | 93.3 |
| Selectivity to styrene (%) | 11.0 | 12.7 |
| Selectivity to benzene (%) | 85.8 | 82.9 |

The above example indicates that catalysts prepared in the above manner show excellent dealkylating properties but were not effective for dehydrogenation purposes.

COMPARISON EXAMPLE 2B

By way of comparison, a catalyst such as the one prepared in Example 1 was used, except that it was not washed with hydrochloric acid, and it was calcined for 1 hour at 600° C. in an oxidizing atmosphere. The residual amount of $Na_2O$ was 0.5%.

The catalyst was tested for the dehydrogenation of ethylbenzene under the following conditions:
Gaseous diluent: $CO_2$
Molar ratio of diluent/ethylbenzene: 16
Temperature: 600° C.
Pressure: atmospheric
LHSV: 0.13
The following results were obtained:

Time after start-up (hrs): 116
Conversion of ethylbenzene (%): 9.21
Selectivity to styrene (%): 86.3

Although the catalyst showed some dehydrogenation properties, the results showed significantly less conversion than in Examples 1 and 2.

COMPARISON EXAMPLE 2C

By way of comparison, the procedure described in Example 1 was used for preparing a catalyst, except that the starting colloidal silica contained 2 wt % $Na_2O$. As a result, the obtained catalyst had a content in residual $Na_2O$ (1.38 wt %) which was too high. It was tested for the dehydrogenation of ethylbenzene; it was observed that the catalyst had no more activity after 102 hours.

COMPARISON EXAMPLE 2D

By way of further comparison, a catalyst prepared by the method described in Example 1 was tested. After calcination under inert atmosphere, this catalyst was washed with hydrochloric acid in order to remove the alkali metal oxide impurities. The resulting catalyst had no significant dehydrogenation activity.

EXAMPLE 3

The catalyst prepared in Example 1 was used for dehydrogenating ethylbenzene under the following conditions:
  gaseous diluent: $N_2$
  molar ratio of diluent/ethylbenzene: 15
  temperature: 600° C.
  pressure: atmospheric
  LHSV: 0.1

After 101 hours run, the conversion of ethylbenzene was only of 23.28%. At this time the $N_2$ diluent was replaced by $CO_2$; the molar ratio of $CO_2$/ethylbenzene was 19. Seventeen hours after the substitution of diluent, the conversion was about 32%, with a selectivity to styrene of 97.3%; 78 hours after the substitution of diluent, the conversion was about 62.21% while the selectivity to styrene was 97.2%, and 460 hours after this substitution the selectivity to styrene was still higher than 90%.

This example shows the advantage of using $CO_2$ as diluent in the dehydrogenation reaction of ethylbenzene to styrene.

EXAMPLE 4

A catalyst was prepared in accordance with the method described in Example 1, except that KOH was added instead of NaOH.

The resulting crystalline silica was calcined at 600° C. under an inert atmosphere of $CO_2$. The crystalline silica had a residual amount of $K_2O$ of 0.66 wt%.

The catalyst was used for dehydrogenating ethylbenzene under the following conditions:
  Gaseous diluent: $CO_2$
  Molar ratio diluent/ethylbenzene: 7
  Temperature: 600° C.
  LHSV: 0.2
  Pressure: atmospheric After 27 hours run, the conversion of ethylbenzene was 20.5%. The selectivity to styrene was 91.3%. After regeneration in a $N_2$ stream containing 2% oxygen, selectivity increased to 94.4% after 64 hours run.

EXAMPLE 5

A catalyst was prepared in accordance with the method described in Example 1, except that KOH was added instead of NaOH. The resulting crystalline silica was washed with HCl and then calcined at 600° C. under an inert atmosphere of $CO_2$. The crystalline silica had a residual amount of $K_2O$ of 0.66 wt%.

The catalyst was used for dehydrogenating ethylbenzene under the following conditions:
  Gaseous diluent: $CO_2$
  Molar ratio diluent/ethylbenzene: 9
  LHSV: 0.2
  Temperature: 600° C.
  Pressure: atmospheric After 74 hours run, the conversion of ethylbenzene was 30.4% with a selectivity to styrene of 95.3%.

While the present invention has been described in various embodiments and illustrated by numerous examples, the person of ordinary skill in the art will appreciate that various modifications, substitutions, omissions, and changes may be made without departing from the spirit thereof.

The embodiments of the invention in which an exclusive property or privilege is claimed are defined as follows:

1. A process for producing vinylaromatic hydrocarbons by dehydrogenation of alkylaromatic hydrocarbons on a crystalline silica which has been calcined under inert atmosphere and which contains from about 0.05 to about 1 wt% of alkali metal oxides.

2. The process of claim 1 wherein the dehydrogenation occurs at a temperature between about 550° C. and about 650° C., at a pressure between about 0.1 and about 50 atmospheres, and at a volume of feed per volume of catalyst per hour between about 0.01 and 0.1.

3. The process of claim 2 wherein the amount of alkali metal oxides is between about 0.05 and 0.5 wt%.

4. The process of claim 3 wherein the alkali metal oxide is sodium oxide.

5. The process of claim 1 wherein the crystalline silica is prepared by
   (i) hydrothermal crystallization of a reaction mixture containing water, a source of silica, and a quaternary ammonium compound having the formula:

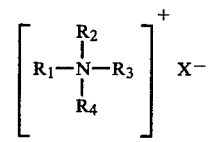

wherein $R_1$, $R_2$, $R_3$ and $R_4$ are alkyl radicals and X is $OH^-$ or the radical of a monovalent acid, at a pH of about 7 to about 14, to form a hydrous crystalline precursor,
   (ii) subsequently washing said precursor with water and then with a strong acid,
   (iii) drying and calcining said precursor in an inert atmosphere to obtain an amount of alkali metal oxides remaining therein between about 0.05 and about 1%.

6. The process of claim 5 wherein the crystalline silica precursor is not submitted to any further washing after the calcining step.

7. The process of claim 6 wherein said calcination is carried out in an inert atmosphere at a temperature between about 450° C. and about 900° C.

8. The process of claim 6 wherein the alkali metal oxide in the crystalline silica results from the silica source itself.

9. The process of claim 1 wherein the crystalline silica is prepared by
(i) hydrothermal crystallization of a reaction mixture containing water, a source of silica, and a quaternary phosphonium compound having the formula:

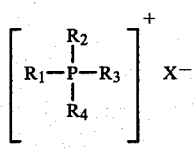

wherein $R_1$, $R_2$, $R_3$ and $R_4$ are alkyl radicals and X is $OH^-$ or the radical of a monovalent acid, at a pH of about 7 to about 14, to form hydrous crystalline precursor,
(ii) subsequently washing said precursor with water and then with a strong acid; and
(iii) drying and calcining said precursor in an inert atmosphere to obtain an amount of alkali metal oxides remaining therein between about 0.05 and about 1%.

10. The process of claim 9 wherein the crystalline silica precursor is not submitted to any further washing after the calcining step.

11. The process of claim 10 wherein said calcination is carried out in an inert atmosphere at a temperature between about 450° C. and about 900° C.

12. The process of claim 6 wherein the molar ratio of gaseous diluent to alkyl aromatic hydrocarbon is between about 1:1 and 25:1.

13. The process of claim 12 wherein the molar ratio of gaseous diluent to alkyl aromatic hydrocarbon is between about 5:1 and 16:1.

14. The process of claim 6 wherein the dehydrogenation reaction is carried out under a pressure between about 0.4 and about 1 atmosphere.

15. The process of claim 1 wherein the dehydrogenation reaction is carried out at a temperature between about 580° C. and about 630° C.

16. The process of claim 1 wherein the dehydrogenation reaction is carried out under a pressure between about 0.3 and about 3 atmospheres.

17. The process of claim 1 wherein the dehydrogenation reaction is carried out in the presence of a diluent selected from the group consisting of helium, nitrogen, carbon dioxide, steam and mixtures thereof.

18. The process of claim 1 wherein the gaseous diluent is carbon dioxide.

19. The process of claim 1 wherein the alkylaromatic hydrocarbon is ethylbenzene.

20. The process of claim 1 wherein the alkylaromatic hydrocarbon is ethyltoluene.

21. The process of claim 1 wherein the alkylaromatic hydrocarbon is isopropybenzene.

22. The process of claim 1 wherein the alkylaromatic hydrocarbon is diethylbenzene.

* * * * *